(12) United States Patent
Kroll

(10) Patent No.: US 7,848,806 B1
(45) Date of Patent: Dec. 7, 2010

(54) VIRTUAL ELECTRODE POLARIZATION FOR SHOCK THERAPY

(75) Inventor: Mark W. Kroll, Crystal Bay, MN (US)

(73) Assignee: Pacesetter, Inc., Sylmar, CA (US)

(*) Notice: Subject to any disclaimer, the term of this patent is extended or adjusted under 35 U.S.C. 154(b) by 777 days.

(21) Appl. No.: 11/359,913

(22) Filed: Feb. 21, 2006

(51) Int. Cl.
*A61N 1/39* (2006.01)
(52) U.S. Cl. .............................. 607/8; 607/5
(58) Field of Classification Search ............ 607/8, 607/5
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,215,083 A * | 6/1993 | Drane et al. | 607/4 |
| 5,346,506 A * | 9/1994 | Mower et al. | 607/7 |
| 5,466,254 A | 11/1995 | Helland | 607/123 |
| 5,476,483 A | 12/1995 | Bornzin et al. | 607/17 |
| 5,522,853 A * | 6/1996 | Kroll | 607/5 |
| 5,564,422 A | 10/1996 | Chen et al. | 128/697 |
| 5,601,608 A * | 2/1997 | Mouchawar | 607/5 |
| 5,899,929 A | 5/1999 | Thompson et al. | 607/28 |
| 6,314,323 B1 | 11/2001 | Ekwall | 607/23 |
| 6,675,042 B2 | 1/2004 | Swerdlow et al. | 607/8 |
| 2002/0035380 A1* | 3/2002 | Rissmann et al. | 607/4 |
| 2003/0163166 A1* | 8/2003 | Sweeney et al. | 607/5 |
| 2004/0106955 A1 | 6/2004 | Swerdlow et al. | 607/4 |

FOREIGN PATENT DOCUMENTS

WO  WO 03/039663 A1  5/2003

OTHER PUBLICATIONS

I.R. Efimov et al., "*Mechanisms of Pacing and Defibrillation—Letters to the Editor*", Europace, Jul. 2003; vol. 5, pp. 243-244.
Michael R. Gold, MD, PhD et al., "*Strength-Duration Relationship for Human Transvenous Defibrillation*", Circulation, Nov. 1997; vol. 96, No. 10, pp. 3517-3520.
K. A. Mowrey et al., "*Kinetics of Defibrillation Shock-Induced Response: Design Implications for the Optimal Defibrillation Waveform*", Europace, Jan. 2002; vol. 4, pp. 27-39.
Gernot Plank Ph.D., et al., "*Defibrillation Depends on Conductivity Fluctuations and the Degree of Disorganization in Reentry Patterns*", J. Cardiovasc Electrophysiol, Feb. 2005; vol. 16, No. 2, pp. 205-216.
Charles Swerdlow, MD et al., "*Determination of the Upper Limit of Vulnerability Using Implantable Cardioverter-Defibrillator Electrograms*", Circulation, Jun. 2003; vol. 107, pp. 3028-3033.

(Continued)

*Primary Examiner*—Michael Kahelin

(57) ABSTRACT

An exemplary method includes configuring a coil electrode as a cathode, calling for delivery of energy to an electrode configuration that includes the coil cathode wherein the energy exceeds one joule, configuring a coil electrode as an anode and, within 10 seconds of the calling, calling for delivery of energy to an electrode configuration that includes the coil anode wherein the energy exceeds one joule. Such an exemplary method may aim to induce fibrillation and to defibrillate tissue. Various other exemplary methods are disclosed as well as various exemplary devices, systems, etc.

3 Claims, 7 Drawing Sheets

OTHER PUBLICATIONS

Charles Swerdlow, MD, *"Implantation of Cardioverter Defibrillators Without Induction of Ventricular Fibrillation"*, Circulation, May 2001; vol. 103, pp. 2159-2164.

Natalia A. Trayanova, Ph.D., et al., *"Virtual Electrode-Induced Positive and Negative Graded Response: New Insights into Fibrillation Induction and Defibrillation"*, J. Cardiovasc Electrophysiol, Jul. 2003; vol. 14, No. 7, pp. 756-763.

Denmanm Russell A. MBBS et al., "Benefit of millisecond waveform durations for patients with high defibrillation thresholds," Heart Rhythm 2006;3:536-541.

Kroll, Mark W. et al., "Present Understanding of Shock Polarity for Internal Defibrillation: The Obvious and Non-Obvious Clinical Implications," PACE. 2006;29:885-891.

* cited by examiner

| # VIRTUAL ELECTRODE POLARIZATION FOR SHOCK THERAPY

TECHNICAL FIELD

Subject matter presented herein generally relates to implantable defibrillation devices. Various exemplary methods, devices, systems, etc., concern induction of arrhythmia and anti-arrhythmia therapy as well as selection or determination of one or more defibrillation shock parameters.

BACKGROUND

Implantable cardiac defibrillators (ICDs) perform two main functions: detecting fibrillation and delivering defibrillation shocks. A variety of issues are associated with use of ICDs. Some issues pertain to the patient while others pertain to the ICD. For example, an ICD should extend patient life and even improve quality of life. On the other hand, an ICD should operate efficiently to conserve its limited power supply.

Efficient operation of an ICD involves delivering defibrillation shocks only when required, delivering an initial defibrillation shock that has a high likelihood of success, and delivering defibrillation shocks at energy levels that are not greatly in excess of a minimum required energy level. The first factor depends largely on fibrillation detection algorithms and ICD capabilities related thereto while the second and third operational factors are interrelated.

Many studies have tried to divine "optimal" shock parameters. While such studies are instructive, a need still exists for better methods to determine or optimize defibrillation shock parameters. Yet further, as described herein, judicious selection of parameters or models or analysis of defibrillation shock information can even yield insight as to cardiac condition.

SUMMARY

An exemplary method includes configuring a coil electrode as a cathode, calling for delivery of energy to an electrode configuration that includes the coil as a cathode wherein the energy exceeds one joule, configuring a coil electrode as an anode and, within 10 seconds of the calling, calling for delivery of energy to an electrode configuration that includes the coil as an anode wherein the energy exceeds one joule. Such an exemplary method aims to induce fibrillation and to defibrillate tissue. Various other exemplary methods are disclosed as well as various exemplary devices, systems, etc.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are optionally implemented in connection with any stimulation device that is configured or configurable to stimulate and/or shock tissue.

Figure 1:
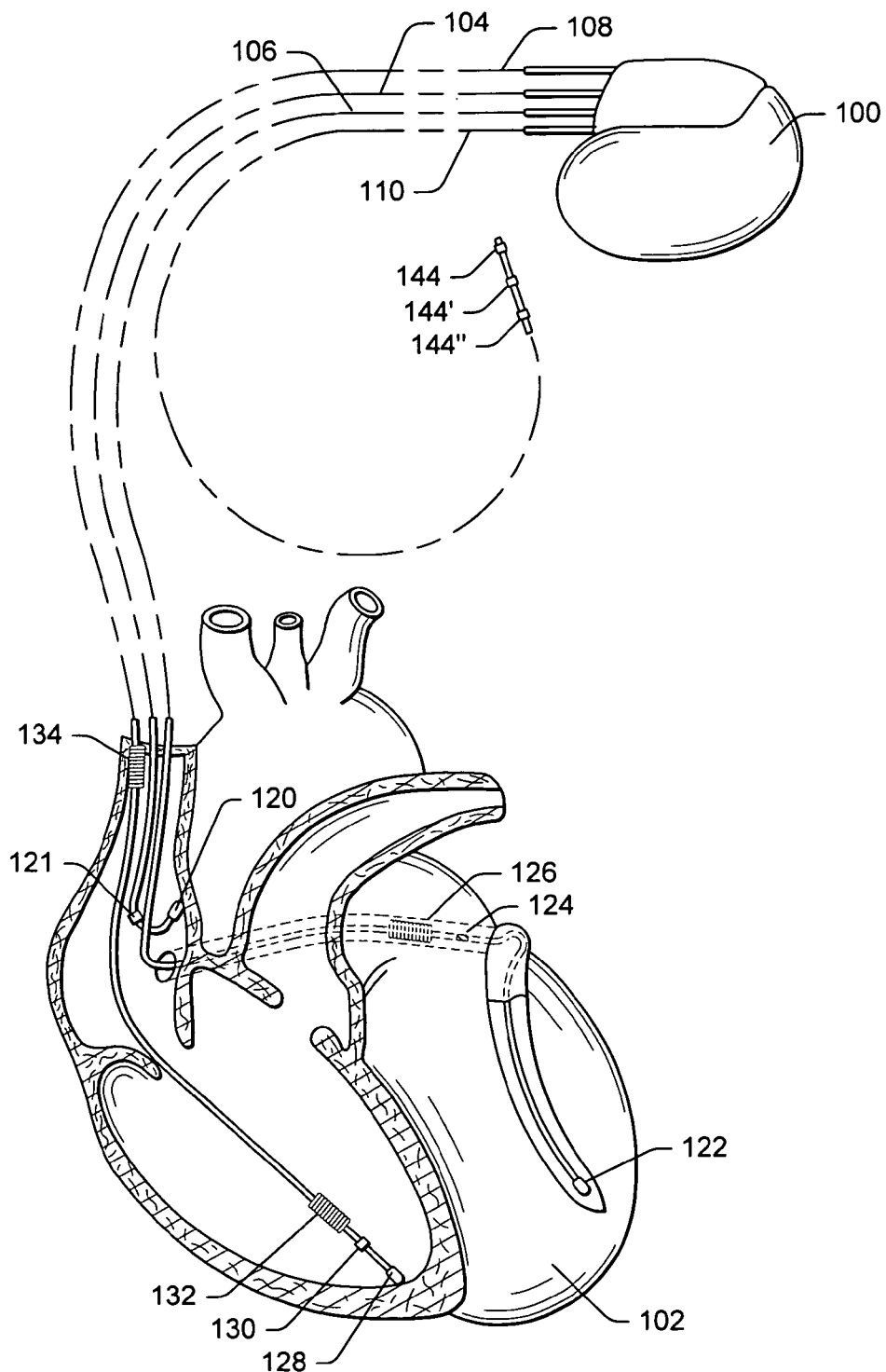
FIG. 1 is a simplified diagram illustrating an exemplary implantable stimulation device in electrical communication with at least three leads implanted into a patient's heart and at least one other lead for delivering stimulation and/or shock therapy. Other examples may include a different number of leads (e.g., fewer or more).

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
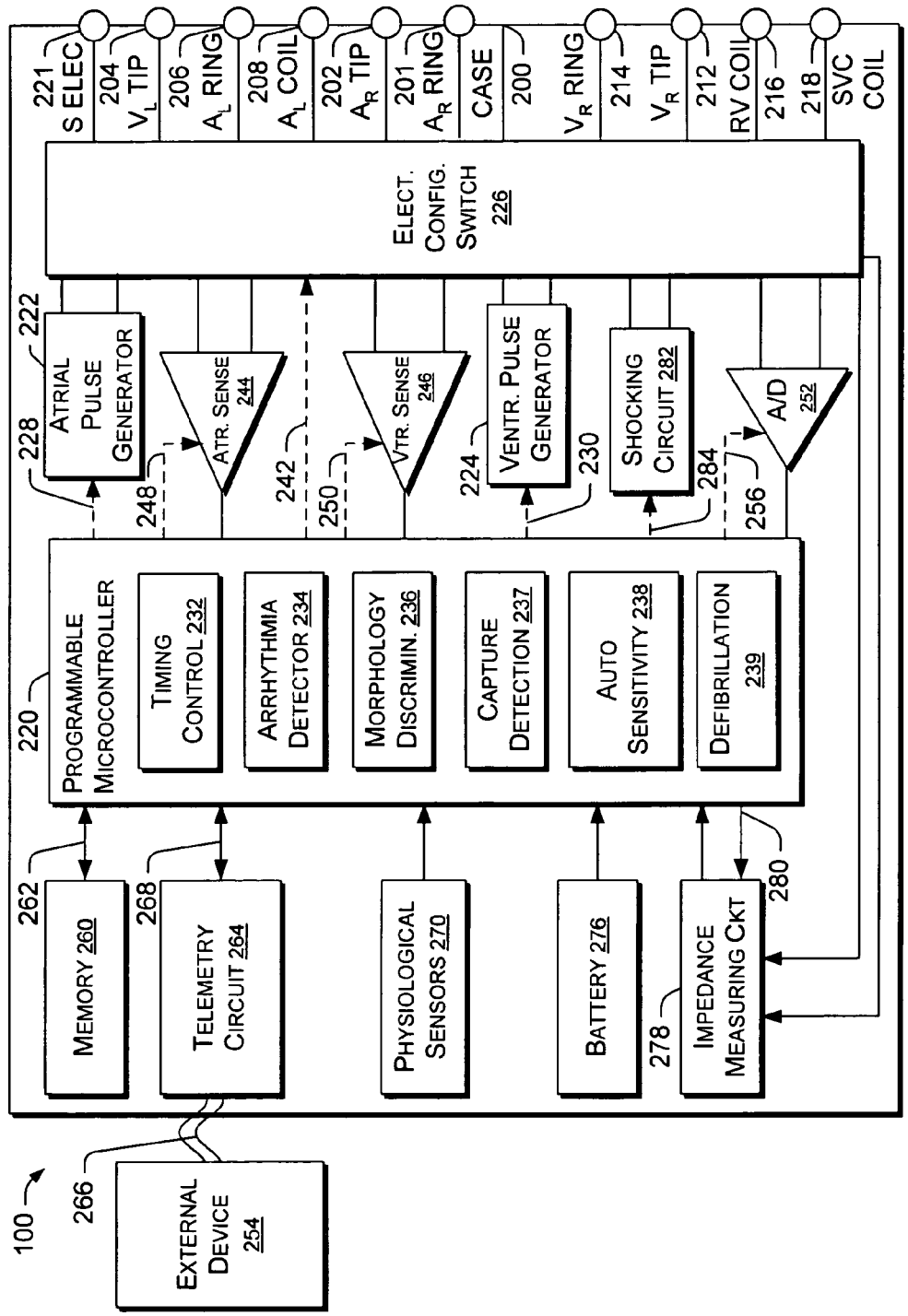
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction delay, or ventricular interconduction delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, an auto sensitivity module 238, a defibrillation module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The defibrillation module 239 may perform a variety of tasks related to defibrillation. Such tasks may include, for example, selection, determination, estimation, etc., of a membrane time constant. Further, the module 239 may aid in ischemia determinations or decisions. The module 239 optionally relies on a variety of information, for example, the module 239 may rely on impedance measurements of a defibrillation shock circuit that includes tissue, fluid, etc., (generally myocardial tissue), cardiac condition, success of prior defibrillations, etc. The module 239 may aid in determining one or more defibrillation shock parameters (e.g., energy, leading edge voltage, duration, phase, waveform type, timing, electrode configuration, etc.). In general, determining a parameter means determining a value, whether the value is an energy, a voltage, a duration, a number of phases, a polarity of delivered energy, an electrode arrangement, etc. The module 239 may operate prior to delivery of a shock or during delivery of a shock or during a shock delivery period (e.g., shock duration).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. As already mentioned, the circuit 278 may provide impedance information to the membrane time constant module 239. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two or more current pathways.

Figure 3:
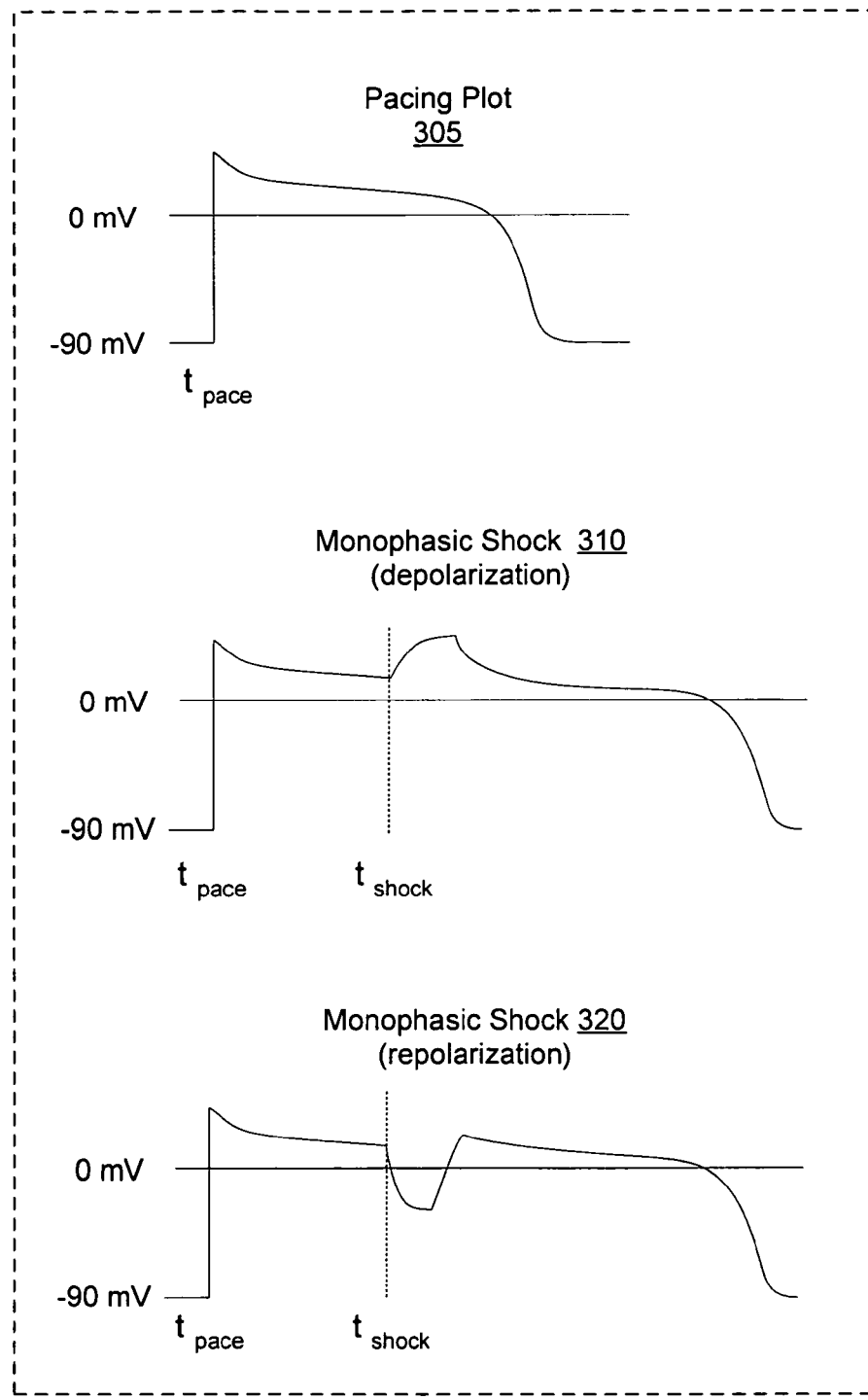
FIG. 3 is a series of plots of potential versus time for a pacing pulse, a depolarization shock and a repolarization or hyperpolarization shock.

FIG. 3 shows various plots 300 of potential versus time. A pacing plot 305 indicates how a cell at a resting potential of about −90 mV is affected by a pacing pulse. According to the plot 305, at a time $t_{pace}$, delivery of a pacing pulse occurs to tissue at a resting potential. At the resting potential, the concentration of sodium ions (Na+) is about 10 times higher outside the membrane than inside whereas the concentration of potassium is about 30 to 50 times higher inside as compared to outside the membrane. In response to the pacing stimulus, the transmembrane potential rises above a threshold value where the sodium and potassium ionic permeabilities of the membrane change. For example, a pacing stimulus delivered with a potential of about +/−4 V is typically sufficient to increase the transmembrane potential to a supra threshold value.

With respect to ion diffusion or transport mechanisms, the sodium ion permeability increases very rapidly at first, allowing sodium ions to flow from outside to inside, making the inside more positive (e.g., reaching a potential of about +20 mV). Thereafter, the potassium ion permeability increases and allows potassium ions to flow from inside to outside. A typical change in membrane potential is about 100 mV. Following activation, Na—K pumps act to restore ion concentrations inside and outside the membrane to their original values (e.g., about −90 mV).

Referring again to the plot 305, when the membrane potential is above the threshold (in this example 0 mV is above the threshold), delivery of another pacing pulse will have little affect on the tissue. Again, pacing pulse energy is typically specified as a potential between two or more electrodes and seldom exceeds +/−10 V. Consequently, the tissue is considered refractory and unaffected by such low stimulation potentials. In contrast, a shock may be delivered at a potential well in excess of +/−10 V (e.g., +/−50 V to +/−800 V or more). In such circumstances, pacing concepts such as relative refractory period and absolute refractory period have little substantive meaning.

Plots 310, 320 indicate changes in tissue potential in response to a shock delivered at a time $t_{shock}$ where $t_{shock} > t_{pace}$ and where $|V_{shock}| >> |V_{pace}|$. In these examples, due to the increased energy (e.g., higher voltage), the tissue responds to the delivered shock where the tissue potential changes from what may be considered a new activation potential to either a lesser or greater value. Depending on the location of the tissue with respect to the two or more shock electrodes (e.g., coil and can, etc.), the tissue may have a positive response (e.g., the plot 310) especially if it is near a cathode or a negative response (e.g., the plot 320) especially if it is near an anode or remain somewhat unchanged at any given moment in time. A strong negative response may cause the tissue to reach a potential less than a normal resting potential (e.g., less than about −90 mV).

The plot 310 indicates that the shock caused the tissue to become less negatively charged or more positively charged. Some refer to this as "depolarization." The plot 320 indicates that the shock caused the tissue to become less positively charged or more negatively charged. Some refer to this as "repolarization." With respect to defibrillation of the heart, consider that fibrillation causes a change in resting potential for the myocardium, consequently, a normal pacing pulse is unlikely to alter or control myocardial behavior. However, a shock of sufficient energy can cause activation regardless of the myocardial potential or potentials. Ideally, the shock synchronizes the fibrillating heart and allows for a return to intrinsic or paced control. The exemplary potential plots 300 serve to demonstrate how a shock can alter the myocardium, regardless of the tissue potential.

Figure 4:
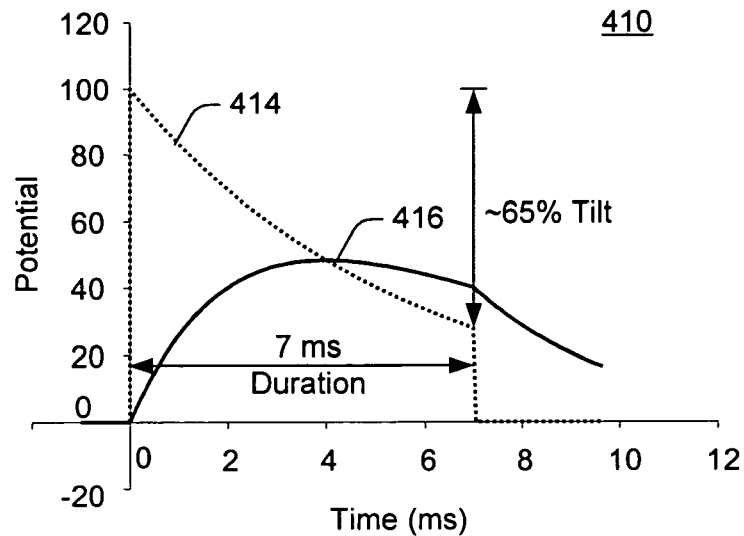
FIG. 4 is a plot of potential versus time for a monophasic defibrillation shock and membrane response thereto and a plot of potential versus time for a biphasic defibrillation shock and membrane response thereto.
Figure 4:
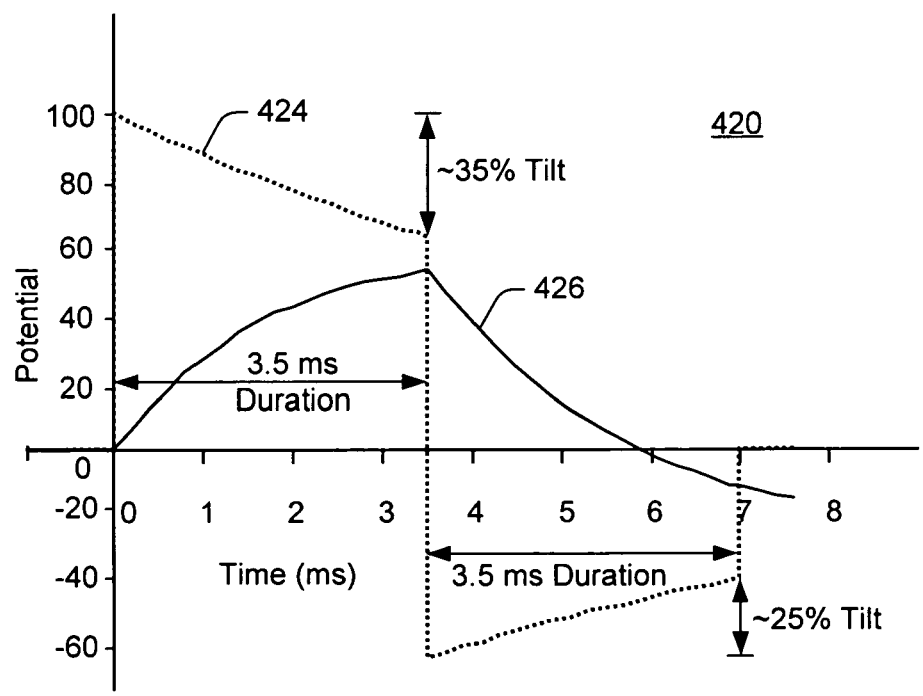

FIG. 4 shows a plot of potential versus time 410 for a defibrillation shock that causes a positive response. More specifically, the plot 410 shows a monophasic, truncated exponential waveform 414 and a corresponding myocardial or membrane response 416. For purposes of explanation, the potential prior to deliver of the shock is set to about 0 mV. While this is typical in a fibrillating heart other values can also be expected. For a negative response, a corresponding plot would be approximately a mirror image of the plot 410 where the monophasic shock 414 is negative.

The waveform or "pulse" 414 may be characterized in part by a parameter called "tilt" and a duration parameter. Tilt is defined as the leading edge voltage at or near an initial time, which is typically the maximum voltage, minus the voltage at the end of the duration divided by the leading edge voltage. Thus, for the example in the plot 410, the waveform has a tilt of approximately 65% while the duration of the shock waveform is about 7 ms. Monophasic, truncated exponential waveforms may be characterized by leading edge voltage, tilt and duration. The leading edge voltage typically depends on resistance or impedance of the tissue into which the shock is delivered and the capacitor(s) used to store charge. Many have described this relationship using an RC circuit, noting that a given tilt and RC circuit parameters may determine the duration, that a given duration and RC parameters may determine tilt, etc.

During delivery of the shock, the membrane is charged and its potential increases. Various optical and electrode mapping studies have revealed the shape of the membrane, which may be characterized by a membrane time constant (τ) according to the following equation:

$$V(t)/V_{max} = (1 - e^{-t/\tau}) \qquad (1)$$

where V(t) is the potential with respect to time t and $V_{max}$ is the maximum potential prior to activation. Such studies indicate that, in humans, the time constant in healthy adults is about 3.5 ms (note that the time constant in the plot is considerably shorter). Models other than that of Eqn. 1 may be used for membrane time constant.

In the plot 410, the data correspond to a capacitor charged to 100% of its voltage and then discharged to deliver the monophasic shock. The cell membrane potential increases during delivery of the shock and reaches a peak at about 4 ms. However, the shock duration (i.e., duration of the monophasic waveform) is greater than the time required by the membrane to reach the peak. Thus, energy is wasted and the membrane subjected to more energy than necessary to achieve the peak potential. Further, the extended duration of the shock is counterproductive as it reduces the final membrane response.

FIG. 4 also shows a plot of potential versus time 420 for another defibrillation shock. More specifically, the plot 420 shows a biphasic, truncated exponential waveform 424 and a corresponding myocardial or membrane response 426. Biphasic, truncated exponential waveforms may be characterized in part by a duration of a first phase and a duration of a second phase.

During delivery of the shock, the membrane is charged (i.e., depolarization) and its potential increases. However, in contrast to the monophasic shock, the second phase of the biphasic shock commences at about the peak (e.g., approximately 3.5 ms) and acts to decrease the membrane potential back to zero.

If during the first phase, a cell is captured, a new activation potential results and the second phase achieves little. If the cell is only marginally charged during the first phase, then the second phase acts to remove the charge and thereby bring the cell to a baseline level. If the cell is electroporated then the second phase, by quickly removing the excess charge sitting on the membrane, acts to quickly "heal" the cell. Of course, in other examples, repolarization may occur first followed by depolarization. More than two phases is not helpful as there is no function left for them to fulfill.

With respect to electroporation, such a process occurs as a result of the reorientation of lipid molecules of a cell's bilayer membrane to form hydrophilic pores in the membrane. The distribution of such pores, both in terms of size and number, determine the electrical properties of the cell membrane. Changes in pore radius are effected by surface tension forces on the pore wall, diffusion of water molecules into and out of the pore and an electric field induced force of expansion. Pore distribution in the presence of an external electric field can be described by Smoluchowski's equation.

In the example of the plot 420, the duration of the second phase, at 3.5 ms, is too long and the membrane is actually discharged and taken slightly negative. This is a suboptimal result noting that a second phase duration of about 2.5 ms would have been optimal.

The plots 410, 420 of FIG. 4 serve to explain various parameters that may be involved in shock therapy. Other parameters may also be used. As described herein, polarity is of primary concern for creating one or more virtual cathodes or one or more virtual anodes (i.e., virtual electrode polarization).

Figure 5:
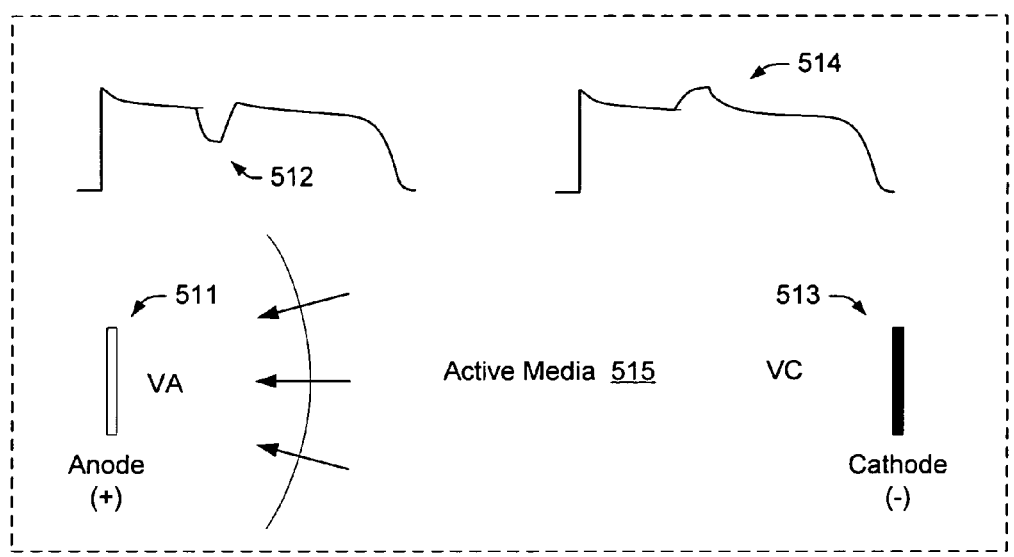
FIG. 5 is a diagram that includes a monophasic anodal shock scenario and a monophasic cathodal shock scenario that can generate virtual electrode polarization.
Figure 5:
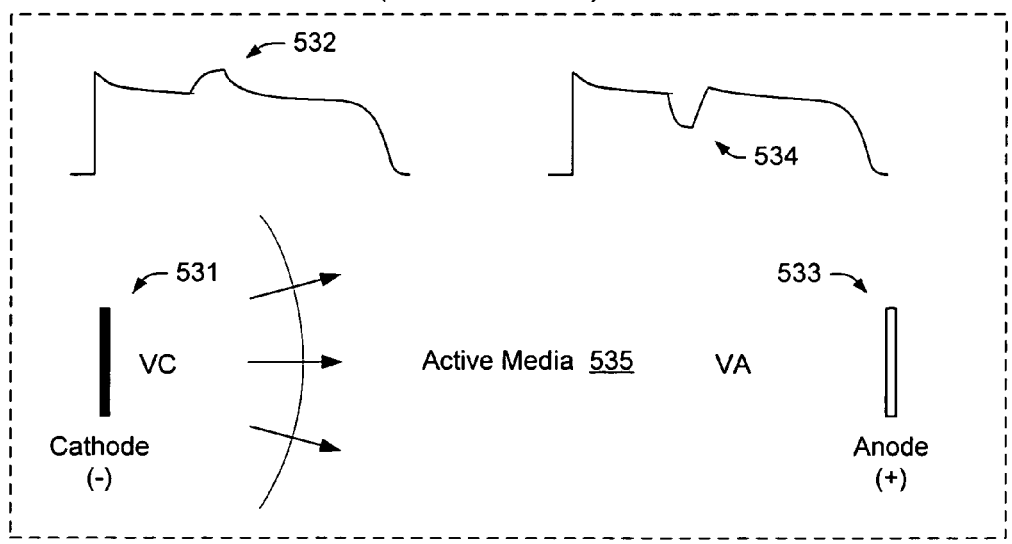

FIG. 5 shows two exemplary scenarios 510, 530 where in each scenario, a monophasic shock is delivered to tissue (e.g., the myocardium). For example, a unipolar configuration may rely on the RV coil electrode 132 of FIG. 1 and the can electrode of the device 100 of FIG. 1. In this example, the coil electrode 132 is positioned adjacent or proximate to the myocardium while the can electrode is remote from the heart (e.g., positioned in a pectoral pocket). Given such a unipolar configuration, the coil electrode 132 may be used as an anode or a cathode where the can electrode is used as a cathode or an anode, respectively.

The monophasic shock scenario 510 includes an anode electrode 511 (positive +) and a cathode electrode 513 (negative −) positioned in active media 515 (e.g., conductive body tissue, fluid, etc.). In other examples, more than one anode or more than one cathode may be used. Upon delivery of a shock using the anode electrode 511 and the cathode electrode 513, active media adjacent and proximate to the anode electrode 511 takes a negative response per the potential plot 512 and active media adjacent and proximate to the cathode electrode 513 has a positive response per the potential plot 514.

As described herein, a virtual anode (VA) is formed adjacent and proximate to the anode electrode 511 and a virtual cathode (VC) is formed adjacent and proximate to the cathode electrode 513 (at least in the cardiac tissue). The extent of such virtual electrodes regions and the boundary or boundaries between such regions may vary. However, where the anode electrode 511 is positioned in a chamber of the heart, a vessel thereof or in the myocardium, then the shock causes formation of a myocardial virtual anode.

Arrows at a boundary proximate to the anode electrode 511 indicate a general wavefront direction, i.e., from cathode to anode or from virtual cathode to virtual anode. Hence, where the anode electrode 511 is positioned in a chamber of the heart, the wavefronts propagate towards this anode electrode.

The monophasic shock scenario 530 includes a cathode electrode 531 (negative −) and an anode electrode 533 (positive +) positioned in active media 535 (e.g., body tissue, fluid, etc.). In other examples, more than one anode or more than one cathode may be used. Upon delivery of a shock using the cathode electrode 531 and the anode electrode 533, active media adjacent and proximate to the cathode electrode 531 takes a positive response per the potential plot 532 and active media adjacent and proximate to the anode electrode 533 has a negative response per the potential plot 534.

As described herein, a virtual cathode (VC) is formed adjacent and proximate to the cathode electrode 531 and a virtual anode (VA) is formed adjacent and proximate to the anode electrode 533 (at least in the cardiac tissue). The extent of such virtual electrodes regions and the boundary or boundaries between such regions may vary. However, where the cathode electrode 531 is positioned in a chamber of the heart, a vessel thereof or in the myocardium, then the shock causes formation of a myocardial virtual cathode.

Arrows at a boundary proximate to the cathode electrode 531 indicate a general wavefront direction, i.e., from cathode to anode or from virtual cathode to virtual anode. Hence, where the cathode electrode 531 is positioned in a chamber of the heart, the wavefronts propagate away from this cathode electrode. In other words, wavefronts are launched away from the cathode electrode. In contrast, in the scenario 510, where the boundary is proximate the anode electrode 511, wavefronts may not travel very far and hence not traverse as much of the myocardium (e.g., consider a cathode can electrode and a RV coil electrode).

For purposes of defibrillation, a care provider or an implantable device may induce fibrillation (e.g., consider the module 239). To induce fibrillation, a stimulus is typically delivered during a vulnerable period of the cardiac cycle (e.g., during a T wave). In such instances, an upper limit to the strength of shocks that induce fibrillation during the vulnerable period (referred to herein as the upper limit of vulnerability or "ULV"), has been shown to exist in both humans and animals.

ULV theory relies on use of premature stimuli to induce ventricular fibrillation during a vulnerable portion of the T wave. Unsuccessful shocks slightly weaker than the energy necessary to defibrillate act to halt activation fronts during fibrillation but, in turn, stimulate regions of myocardium during a vulnerable period, which gives rise to new activation fronts that reinitiate fibrillation. Stimuli delivered at energies above the upper limit defibrillate by extinguishing fibrillation activation fronts without causing new activation fronts that can reinitiate fibrillation.

Therefore, according to the ULV theory, two requirements are necessary for a shock to defibrillate the myocardium: (i) the shock must squelch activation fronts in a manner such that fibrillation cannot reoccur after the shock and (ii) the shock must not initiate new activation fronts that reinitiate fibrillation where the latter is more determinative of the DFT.

In sum, the ULV is the weakest stimulus that does not induce VF when delivered during a vulnerable period and ULV has been shown to correlates closely with the minimum shock energy that defibrillates reliably (e.g., DFT). ULV has been used as a basis for programming implantable cardioverter defibrillator (ICD) shocks (see, e.g., Swerdlow et al., "Determination of the Upper Limit Vulnerability Using Implantable Cardioverter-Defibrillator Electrograms", *Circulation*. 2003; 107: 3028).

As described herein, an exemplary method relies on defibrillation shocks delivered using one or more anode electrodes positioned in a chamber, vessel or tissue of the heart and one or more cathode electrodes, which may be positioned remote from the heart. Such a method may be referred to as an "anodal defibrillation" method where a so-called "anodal shock" is delivered to the heart. Again, given the requirement that a defibrillation shock should not initiate new activation fronts that reinitiate fibrillation, such an exemplary configuration is practical.

An exemplary method relies on ULV determination whereby stimulation is delivered using one or more cathode electrodes positioned in a chamber, vessel or tissue of the heart and one or more anode electrodes, which may be positioned remote from the heart. In such an example, wavefronts are launched away from the cathode electrode and hence have a greater chance of initiating fibrillation (see, e.g., scenario 530). In contrast, in the scenario 510, where the boundary is proximate the anode electrode 511, wavefronts may not travel very far and hence not traverse as much of the myocardium and hence not initiate fibrillation as readily as in the scenario 530.

An exemplary method relies on initiation of fibrillation to determine a defibrillation energy where stimulation to initiate the fibrillation relies on one or more cathode electrodes positioned in a chamber, vessel or tissue of the heart and where the shock to defibrillate relies on one or more anode electrodes positioned in a chamber, vessel or tissue of the heart. For example, the initiation may use a RV coil electrode as a cathode and a can electrode as an anode and the defibrillation may use the RV coil electrode as an anode and the can electrode as a cathode. Such an exemplary method may rely on monophasic stimulation to initiate fibrillation and multiphasic stimulation for defibrillation.

A recent study by Plank et al., "Defibrillation depends on conductivity fluctuations and the degree of disorganization in reentry patterns", *J Cardiovasc Electrophysiol*. 2005 February; 16(2): 205-216, reported that defibrillation success can depend on fibrillation characteristics. In particular, the results of the study of Plank et al. suggest that the level of the small-scale conductivity fluctuations is a very important factor in defibrillation where a higher variation significantly lowers the required shock strength. Further, the study states that success also heavily depends on the level of organization of the fibrillatory episode where higher levels of disorganization require higher shock strengths to defibrillate.

An exemplary method initiates fibrillation using a configuration of electrodes with a first polarity and initiates defibrillation using the configuration of electrodes with a second polarity where the second polarity is opposite the first polarity. For example, the configuration may use a first polarity where a coil electrode is a cathode and a can electrode is an anode and a second polarity where the coil electrode is an anode and the can electrode is the cathode. Analysis of results of such an exemplary method optionally accounts for travel distance of wavefronts from a virtual electrode region (e.g., virtual cathode or virtual anode) to another region.

Figure 6:
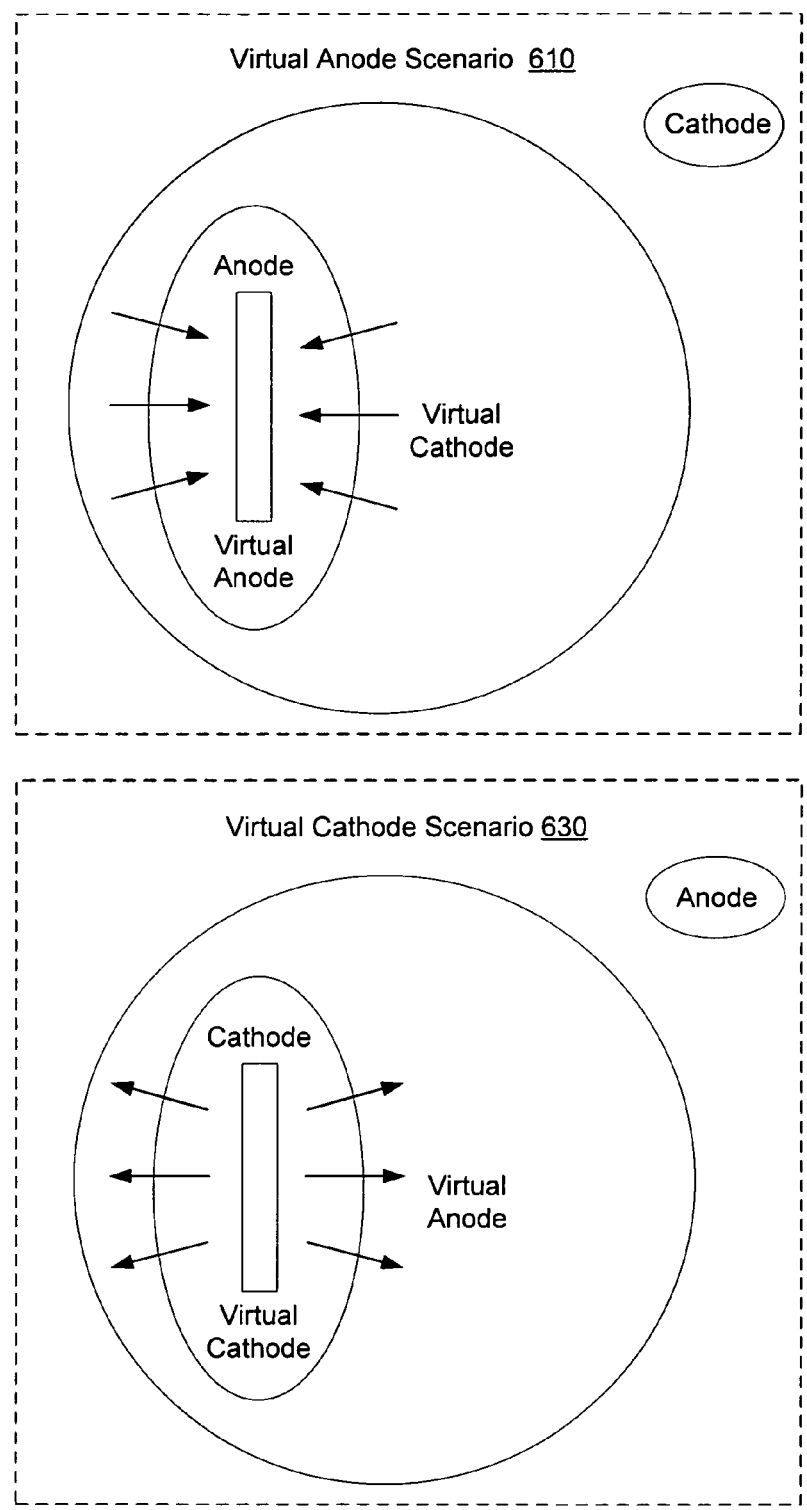
FIG. 6 is a diagram that includes a virtual anode region around an anode and a virtual cathode region around a cathode.

FIG. 6 shows two exemplary scenarios 610, 630 where a virtual anode region and a virtual cathode region are shown. As already mentioned, wavefront movements in these two scenarios differ. As described herein, the exemplary scenario 630 is more effective at inducing fibrillation in tissue (e.g., proarrhythmic) whereas the exemplary scenario 610 is more effective at defibrillating tissue.

With respect to defibrillation, an exemplary electrode configuration aims to create a virtual anode in cardiac tissue. Such a virtual anode may be tailored using one or more electrodes and optionally relies on past success or information about a patients heart. For example, if a particular region is known to be an origin for VF, then the electrode configuration may be selected to create a virtual anode for this VF initiating region. Upon delivery of stimulation (e.g., shock) to this region, to thereby create a virtual anode, wavefronts converge on this region and enter the region to return this region to a non-arrhythmic state.

Figure 7:
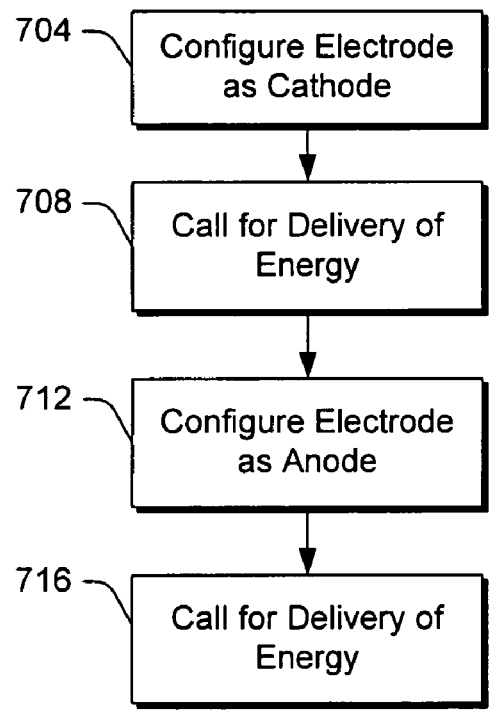
FIG. 7 is a diagram of an exemplary method that aims to induce an arrhythmia (e.g., fibrillation) and to delivery anti-arrhythmia therapy (e.g., defibrillation).

FIG. 7 shows an exemplary method 700 that relies on creating virtual electrode polarization. A configuration block 704 configures an electrode as a cathode. A call block 708 calls for delivery of energy whereby creation of a virtual cathode region occurs upon delivery of the energy, for example, in a region surrounding the cathode. Such a call may aim to induce fibrillation, for example, via wavefronts emanating from the virtual cathode region. Another configuration block 712 configures an electrode as an anode (e.g., the aforementioned electrode or another electrode). A call block 716 calls for delivery of energy to defibrillate the tissue.

The exemplary method 700 of FIG. 7 optionally includes configuring a coil electrode as a cathode, calling for delivery of energy to an electrode configuration that includes the coil cathode wherein the energy exceeds one joule, configuring a coil electrode as an anode and, within 10 seconds of the calling, calling for delivery of energy to an electrode configuration that includes the coil anode wherein the energy exceeds one joule. In such a method, the calling for delivery of energy to an electrode configuration that includes the coil cathode may call for a monophasic waveform while the calling for delivery of energy to an electrode configuration that includes the coil anode may call for a biphasic waveform. While this particular example mentions specific waveforms, in general, the calling for delivery of energy to an electrode configuration that includes the coil cathode may include calling for a waveform and the calling for delivery of energy to an electrode configuration that includes the coil anode may include calling for a different waveform.

The exemplary method 700 of FIG. 7 is optionally used to determine a defibrillation threshold. Additional logic or other instructions are optionally in the form of one or more computer-readable media with process executable instructions.

An exemplary method includes configuring a coil electrode as a cathode and calling for delivery of energy in the form of a monophasic waveform to an electrode configuration that includes the coil cathode wherein the energy exceeds one joule and wherein the calling aims to induce fibrillation. Such a method may further include configuring the coil electrode as an anode and calling for delivery of energy to an electrode configuration that includes the coil anode wherein the energy exceeds one joule.

As for various other exemplary methods, the calling for delivery of energy to an electrode configuration that includes the coil anode may call for delivery of energy in the form of a biphasic waveform that aims to defibrillate tissue. Further, the calling for delivery of energy to an electrode configuration that includes the coil anode may occur within about 10 seconds of the calling for delivery of energy in the form of a monophasic waveform to an electrode configuration that includes the coil cathode.

An exemplary method includes configuring a coil electrode as a cathode and a can electrode as an anode, calling for delivery of energy in excess of approximately one joule via the coil cathode and the can anode, reconfiguring the coil electrode to a coil anode and the can electrode to a can cathode and calling for delivery of energy via the coil anode and the can cathode. As already mentioned, waveforms for the energies may differ (e.g., monophasic, multiphasic) as well as the energies (e.g., current, voltage, etc.).

In various examples, the calling for delivery of energy may act to deliver energy during a vulnerable period, for example, where the vulnerable period corresponds to at least a portion of a T wave.

In various examples, one or more tilts, durations, etc., relating to delivery of energy may be selected, for example, to induce arrhythmia or to treat an arrhythmic condition. Also an exemplary method may include detecting fibrillation and calling for defibrillation through delivery of energy.

An exemplary implantable device (see, e.g., the device 100 of FIG. 1) includes a power source, one or more capacitors chargeable by the power source and control logic to call for charging of the one or more capacitors, to configure a coil electrode as a cathode, to call for delivery of energy from the one or more capacitors to an electrode configuration that includes the coil cathode wherein the energy exceeds one joule, to configure a coil electrode as an anode and to call for delivery of energy from the one or more capacitors to an electrode configuration that includes the coil anode wherein the energy exceeds one joule.

Although exemplary methods, devices, systems, etc., have been described at times in language specific to structural features or methodological acts, it is to be understood that the subject matter defined in the appended claims is not necessarily limited to the specific features or acts described. Rather, the specific features and acts are disclosed as exemplary forms of implementing various claimed subject matter.

The invention claimed is:

1. A method to determine a defibrillation energy comprising:
   configuring a coil electrode of a transvenous lead as a cathode to induce fibrillation of a heart;
   inducing fibrillation of the heart by calling for delivery of energy during a T wave in the form of a monophasic waveform to an electrode configuration that includes the coil cathode wherein the energy exceeds one joule;
   inducing defibrillation of the induced fibrillation of the heart by configuring the coil electrode as an anode and calling for delivery of energy to an electrode configuration that includes the coil anode wherein the energy exceeds one joule; and
   determining a defibrillation energy threshold based on said inducing fibrillation and inducing defibrillation.

2. The method of claim 1 wherein the calling for delivery of energy to an electrode configuration that includes the coil anode occurs within 10 seconds of the calling for delivery of energy in the form of a monophasic waveform to an electrode configuration that includes the coil cathode.

3. The method of claim 1 wherein the electrode configuration that includes the coil cathode comprises a can electrode as an anode.

* * * * *